US011651512B2

(12) United States Patent
Pak et al.

(10) Patent No.: US 11,651,512 B2
(45) Date of Patent: May 16, 2023

(54) MEASUREMENT DEVICE AND MEASUREMENT METHOD FOR LEFT ATRIUM THICKNESS OF HEART

(71) Applicant: INDUSTRY-ACADEMIC COOPERATION FOUNDATION YONSEI UNIVERSITY, Seoul (KR)

(72) Inventors: Hui-Nam Pak, Seoul (KR); Byounghyun Lim, Seoul (KR); Oh Seok Kwon, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 164 days.

(21) Appl. No.: 17/424,011

(22) PCT Filed: Jan. 30, 2020

(86) PCT No.: PCT/KR2020/001380
§ 371 (c)(1),
(2) Date: Jul. 19, 2021

(87) PCT Pub. No.: WO2020/159234
PCT Pub. Date: Aug. 6, 2020

(65) Prior Publication Data
US 2022/0084233 A1    Mar. 17, 2022

(30) Foreign Application Priority Data
Feb. 1, 2019  (KR) .......................... 10-2019-0014002

(51) Int. Cl.
*G06T 7/62* (2017.01)
*A61B 18/00* (2006.01)

(52) U.S. Cl.
CPC ...... *G06T 7/62* (2017.01); *G06T 2207/10081* (2013.01); *G06T 2207/20024* (2013.01); *G06T 2207/30048* (2013.01)

(58) Field of Classification Search
CPC ............ G06T 7/62; G06T 2207/10081; G06T 2207/20024; G06T 2207/30048;
(Continued)

(56) References Cited

U.S. PATENT DOCUMENTS

| | | |
|---|---|---|
| 2004/0153128 A1 | 8/2004 | Suresh et al. |
| 2008/0292169 A1 | 11/2008 | Wang et al. |
| 2011/0118596 A1 | 5/2011 | Vining et al. |
| 2017/0004618 A1* | 1/2017 | Voigt .................. A61B 5/1076 |
| 2019/0328275 A1* | 10/2019 | Shmayahu ............ G06T 7/0012 |

FOREIGN PATENT DOCUMENTS

| | | |
|---|---|---|
| KR | 10-2011-0077795 A | 7/2011 |
| KR | 10-2011-0077795 * | 4/2012 |

(Continued)

OTHER PUBLICATIONS

Search Report, dated May 7, 2020, for International Application No. PCT/KR2020/001380.
(Continued)

*Primary Examiner* — Siamak Harandi
(74) *Attorney, Agent, or Firm* — LRK Patent Law Firm

(57) ABSTRACT

A method by which a left atrial wall thickness measurement device for the heart measures the left atrial wall thickness of the heart, according to one embodiment of the present invention, can simply, quickly, and accurately measure the thickness of the left atrium of the heart with only a simple input of a user so as to also derive the optimum effect of a radiofrequency catheter ablation procedure, and measures the thickness of the left atrium of the heart by using, without a separate additional inspection, computed tomography, (Continued)

which is relatively inexpensive and is performed for most patients with arrhythmia, thereby minimizing the financial burden on a patient.

12 Claims, 18 Drawing Sheets

(58) Field of Classification Search
CPC ......... G06T 7/0012; G06T 2207/30101; A61B 18/1492; A61B 2018/00351; A61B 2018/00577; A61B 2034/105; A61B 2090/061; A61B 6/481; A61B 6/5217; A61B 6/032; A61B 6/503
See application file for complete search history.

(56) References Cited

FOREIGN PATENT DOCUMENTS

| KR | 10-2012-0050595 A | 5/2012 |
| KR | 10-2018-0108210 A | 10/2018 |

OTHER PUBLICATIONS

Written Opinion, dated May 7, 2020, for International Application No. PCT/KR2020/001380.

EPO Office Action, dated Sep. 13, 2022, for European Patent Application No. 20747643.3 which corresponds to the above-identified U.S. application.

* cited by examiner

MEASUREMENT DEVICE AND MEASUREMENT METHOD FOR LEFT ATRIUM THICKNESS OF HEART

CROSS-REFERENCE TO RELAYED APPLICATIONS

The present application is a U.S. National Phase entry from International Application No. PCT/KR2020/001380, filed on Jan. 30, 2020, which claims priority to Korean Patent Application No. 10-2019-0014002, filed on Feb. 1, 2019, the disclosure of which is incorporated by reference herein in their entirety.

TECHNICAL FIELD

The present invention relates to a measurement device and method for the left atrial wall thickness of the heart. More particularly, the present invention relates to a measurement device and method for the left atrial wall thickness of the heart that is capable of predetermining the intensity of radiofrequency catheter ablation using computed tomography (CT) images.

BACKGROUND ART

Heart arrhythmias occur when the electrical impulses in the heart don't work properly or don't be transferred well, thereby causing the heart to beat too fast, too slow or irregularly. This may result in sudden death or stroke.

Radiofrequency catheter ablation, which is a procedure that is performed to treat the heart arrhythmias, scars tissue in the heart to block the electrical conduction of the heart, but it is difficult to pre-recognize whether any part of the heart is subjected to the radiofrequency catheter ablation with any degree of intensity.

The problems occurring in the radiofrequency catheter ablation can be solved if the thickness of the heart is pre-measured accurately. A part where a low thickness is measured is subjected to radiofrequency catheter ablation at a relatively low intensity, and contrarily, a part where a high thickness is measured is subjected to radiofrequency catheter ablation at a relatively high intensity, so that optimal effects can be obtained. Accordingly, many studies on the methods for measuring the thickness of the heart through various means have been recently conducted. In this case, the thickness of the heart has to be measured simply and quickly, and further, the measured results have to be accurate. Besides, the financial load of the medical expense of a patient has to be minimized.

So as to solve the problems as mentioned above, accordingly, the present invention relates to a device and method for measuring the thickness of the heart, more particularly the thickness of the left atrium as a region from which the heart arrhythmia occurs.

DISCLOSURE

Technical Problem

Accordingly, the present invention has been made to solve the above-mentioned problems, and it is an object of the present invention to provide a measurement device and method for the left atrial wall thickness of the heart that is capable of simply and quickly measuring the left atrial wall thickness prior to radiofrequency catheter ablation.

It is another object of the present invention to provide a measurement device and method for the left atrial wall thickness of the heart that is capable of obtaining accurately measured results for the left atrial wall thickness prior to radiofrequency catheter ablation.

It is yet another object of the present invention to provide a measurement device and method for the left atrial wall thickness of the heart that is capable of measuring the left atrial wall thickness prior to radiofrequency catheter ablation, while minimizing the financial burden of the medical expense of a patient.

The technical problems to be achieved through the present invention are not limited as mentioned above, and other technical problems not mentioned herein will be obviously understood by one of ordinary skill in the art through the following description.

Technical Solution

To accomplish the above-mentioned objects, according to one aspect of the present invention, there is provided a measurement method for the left atrial wall thickness of the heart through a left atrial wall thickness measurement device, the method including the steps of: (a) extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted; (b) extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted; (c) calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors; (d) correcting the Hounsfield numbers provided to the plurality of pixels corresponding to the directions of the three-dimensional normal vectors for the plurality of pixels through interpolation; and (e) calculating the left atrial wall thickness of the heart by applying full width at half maximum (FWHM) to the corrected Hounsfield numbers.

According to an embodiment of the present invention, the step (a) may include the steps of: (a-1) extracting the plurality of pixels having a given value or more in a histogram of the Hounsfield numbers applied to the plurality of pixels included in the Nth CT image; (a-2) applying the plurality of pixels extracted to a Sobel filter to output an area corresponding to 0 as a Sobel filter output value on an area to which a contrast medium is transmitted to a plurality of circular shapes on the Nth CT image; and (a-3) extracting any one of the plurality of circular shapes as the left atrial outline of the heart through the reception of user input.

According to an embodiment of the present invention, further, the step (a) may include the step of, after the step (a-3), extracting and blocking the mitral valve connecting the left atrium and the left ventricle of the heart through the reception of user input.

According to an embodiment of the present invention, the step (b) may include the steps of: (b-1) searching a plurality of pixels within a given range with respect to the coordinates of the plurality of pixels corresponding to the left atrial outline extracted in the Nth CT image in any one or more images of the first, N−1th, N+1th, and Mth CT images; and (b-2) extracting the plurality of pixels corresponding to the left atrial outline from any one or more images of the first, N−1th, N+1th, and Mth CT images, using the coordinates of the plurality of pixels within the given range searched and the coordinates of the plurality of pixels corresponding to the left atrial outline extracted in the Nth CT image to calculate the two-dimensional normal vectors for the plurality of pixels extracted.

According to an embodiment of the present invention, the given range is any one of one pixel (3*3), two pixels (5*5), and two pixels (5*3) in left and right sides and one pixel in up and down sides in every direction with respect to the coordinates of the plurality of pixels corresponding to the left atrial outline extracted in the Nth CT image.

According to an embodiment of the present invention, the step (c) may include the steps of: (c-1) searching a second pixel and a third pixel closest to a first pixel as any one of the plurality of pixels corresponding to the left atrial outline extracted in the Nth CT image and searching a fourth pixel closest to the first pixel in the N−1th CT image and a fifth pixel closest to the first pixel in the N+1th CT image along the two-dimensional normal vector calculated for the first pixel; (c-2) searching a sixth pixel and a seventh pixel closest to the fourth pixel in the N−1th CT image and searching an eighth pixel and a ninth pixel closest to the fifth pixel in the N+1th CT image; and (c-3) calculating the normal vectors for eight triangles formed by the first pixel to the ninth pixel and adding the eight normal vectors calculated to calculate the three-dimensional normal vector for the first pixel.

According to an embodiment of the present invention, further, the step (c) may include the step of performing the steps (c-1) to (c-3) for the plurality of pixels corresponding to the left atrial outline extracted in the Nth CT image and for the plurality of pixels corresponding to the left atrial outline extracted in any one or more images of the first, N−1th, N+1th, and Mth CT images, except the first pixel.

According to an embodiment of the present invention, the interpolation at the step (d) is trilinear interpolation.

According to an embodiment of the present invention, the step (e) may include the steps of: (e-1) applying the FWHM to the plurality of pixels to calculate the number of pixels extracted; and (e-2) multiplying the number of pixels by a length of pixel to calculate the left atrial wall thicknesses at the plurality of pixels.

According to an embodiment of the present invention, the length of pixel is 0.4434 mm.

To accomplish the above-mentioned objects, according to another aspect of the present invention, there is provided a measurement device for the left atrial wall thickness of the heart, the device including: one or more processors; a network interface; a memory for loading computer programs executed by the processors; and a storage for storing large scale network data and the computer programs, wherein the computer programs may perform: an operation (a) for extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted; an operation (b) for extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted; an operation (c) for calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors; an operation (d) for correcting the Hounsfield numbers provided to the plurality of pixels corresponding to the directions of the three-dimensional normal vectors for the plurality of pixels through interpolation; and an operation (e) of calculating the left atrial wall thickness of the heart by applying full width at half maximum (FWHM) to the corrected Hounsfield numbers.

To accomplish the above-mentioned objects, according to yet another aspect of the present invention, there is provided a computer program stored in a medium and combined to a computing device to perform the steps of: (a) extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted; (b) extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted; (c) calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors; (d) correcting the Hounsfield numbers provided to the plurality of pixels corresponding to the directions of the three-dimensional normal vectors for the plurality of pixels through interpolation; and (e) calculating the left atrial wall thickness of the heart by applying full width at half maximum (FWHM) to the corrected Hounsfield numbers.

Advantageous Effects

According to the present invention, the measurement device and method for the left atrial wall thickness of the heart can measure the left atrial wall thickness of the heart simply, quickly and accurately, just using the simple input of the user, thereby providing optimal effects in radiofrequency catheter ablation.

Moreover, the measurement device and method for the left atrial wall thickness of the heart according to the present invention can measure the left atrial wall thickness of the heart using the CT images performed for most patients with heart arrhythmia at a relatively low expense, without any additional test, thereby minimizing the financial burden of the medical expense of the patients.

The beneficial effects of the invention are not limited as mentioned above, and it should be understood to those skilled in the art that the beneficial effects of the invention may include another beneficial effects as not mentioned above from the detailed description of the present invention.

MODE FOR INVENTION

Figure 1:
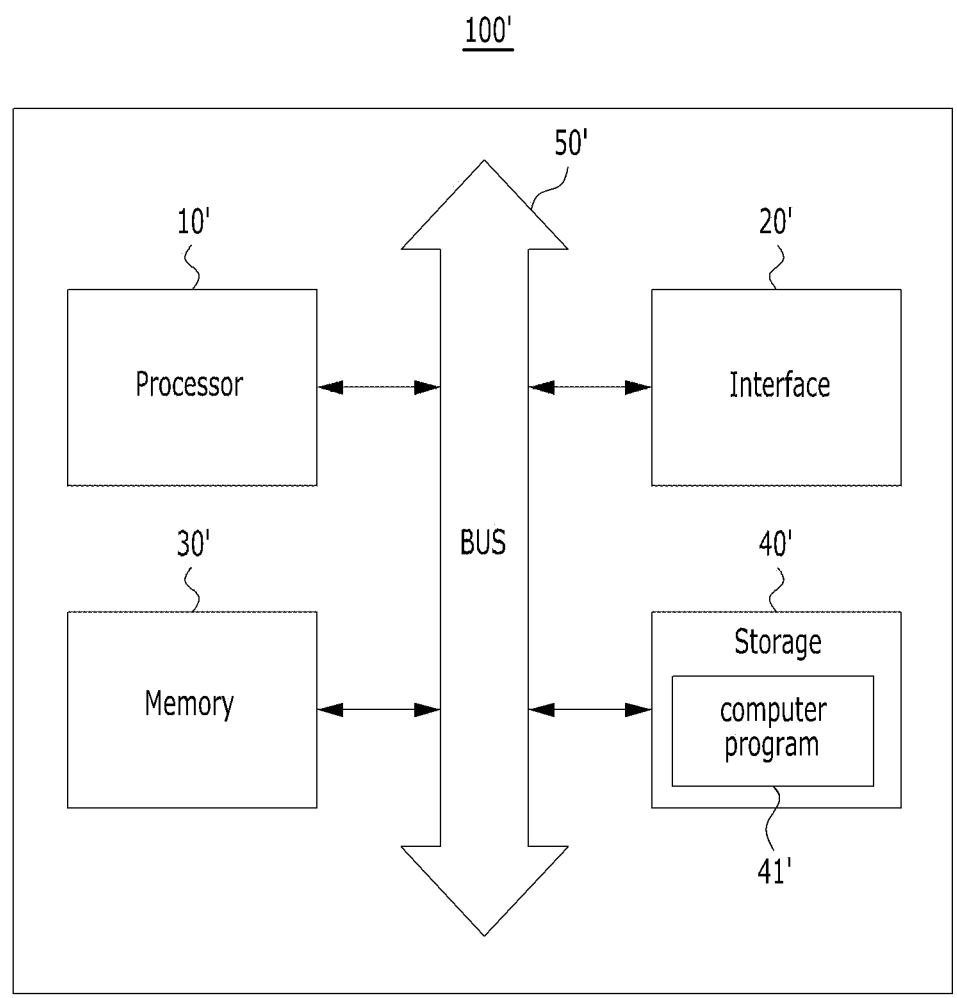
FIG. 1 is a block diagram showing a configuration of a measurement device for the left atrial wall thickness of the heart according to a first embodiment of the present invention.

Hereinafter, the present invention will now be described in detail with reference to the attached drawings. Objects, characteristics and advantages of the present invention will be more clearly understood from the detailed description as will be described below and the attached drawings. Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. In the description, it should be noted that the parts corresponding to those of the drawings are indicated by corresponding reference numerals.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification. Terms used in this application are used to only describe specific exemplary embodiments and are not intended to restrict the present invention. An expression referencing a singular value additionally refers to a corresponding expression of the plural number, unless explicitly limited otherwise by the context.

In this application, terms, such as "comprise", "include", or 'have', are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

FIG. 1 is a block diagram showing a configuration of a measurement device 100 for the left atrial wall thickness of the heart according to a first embodiment of the present invention.

However, the first embodiment of the present invention is just a preferred embodiment to accomplish the objects of the present invention. If necessary, some of the parts constituting the measurement device 100 may be deleted, or new parts may be added. Of course, the functions executed by one part may be executed together with another part.

The measurement device 100 for the left atrial wall thickness of the heart according to the first embodiment of the present invention includes a processor 10, a network interface 20, a memory 30, a storage 40, and a data bus 50 for connecting them to one another.

The processor 10 controls all of the operations of the respective parts. The processor 10 is any one selected from a central processing unit (CPU), a micro processor unit (MPU), a micro controller unit (MCU), and a processor in the form widely known in the art. Further, the processor 10 can perform an operation for at least one application or program for performing a measurement method for the left atrial wall thickness of the heart according to a second embodiment of the present invention.

The network interface 20 supports wireless or wired internet communication of the measurement device 100 for the left atrial wall thickness of the heart according to the first embodiment of the present invention and other known communication, as well. Accordingly, the network interface 20 includes a communication module.

The memory 30 stores all kinds of data, commands and/or information and loads one or more computer programs from the storage 40 to perform the measurement method for the left atrial wall thickness of the heart according to the second embodiment of the present invention. As shown in FIG. 1, a random access memory (RAM) is provided as the memory 30, but of course, various storage media may be used as the memory 30.

The storage 40 non-temporarily stores one or more computer programs 41 and large scale network data. The storage 40 may be any one selected from a non-volatile memory such as a read only memory (ROM), erasable programmable ROM (EPROM), electrically erasable programmable ROM (EEPROM), and flash memory, a hard disc, a detachable disc, and a computer readable recording medium well known in the art.

The computer programs 41 are loaded to the memory 30 and then perform an operation for extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted, an operation for extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted, an operation for calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors, an operation for correcting the Hounsfield numbers provided to the plurality of pixels corresponding to the directions of the three-dimensional normal vectors for the plurality of pixels through interpolation, and an operation of calculating the left atrial wall thickness of the heart by applying full width at half maximum (FWHM) to the corrected Hounsfield numbers.

The operations performed by the computer programs 41, as mentioned above, are included in one of the functions of the computer programs 41, and they will be described in detail in the explanation of the measurement method for the left atrial wall thickness of the heart according to the second embodiment of the present invention.

Now, the measurement method for the left atrial wall thickness of the heart according to the second embodiment of the present invention will be explained with reference to FIGS. 2 to 18.

Figure 2:
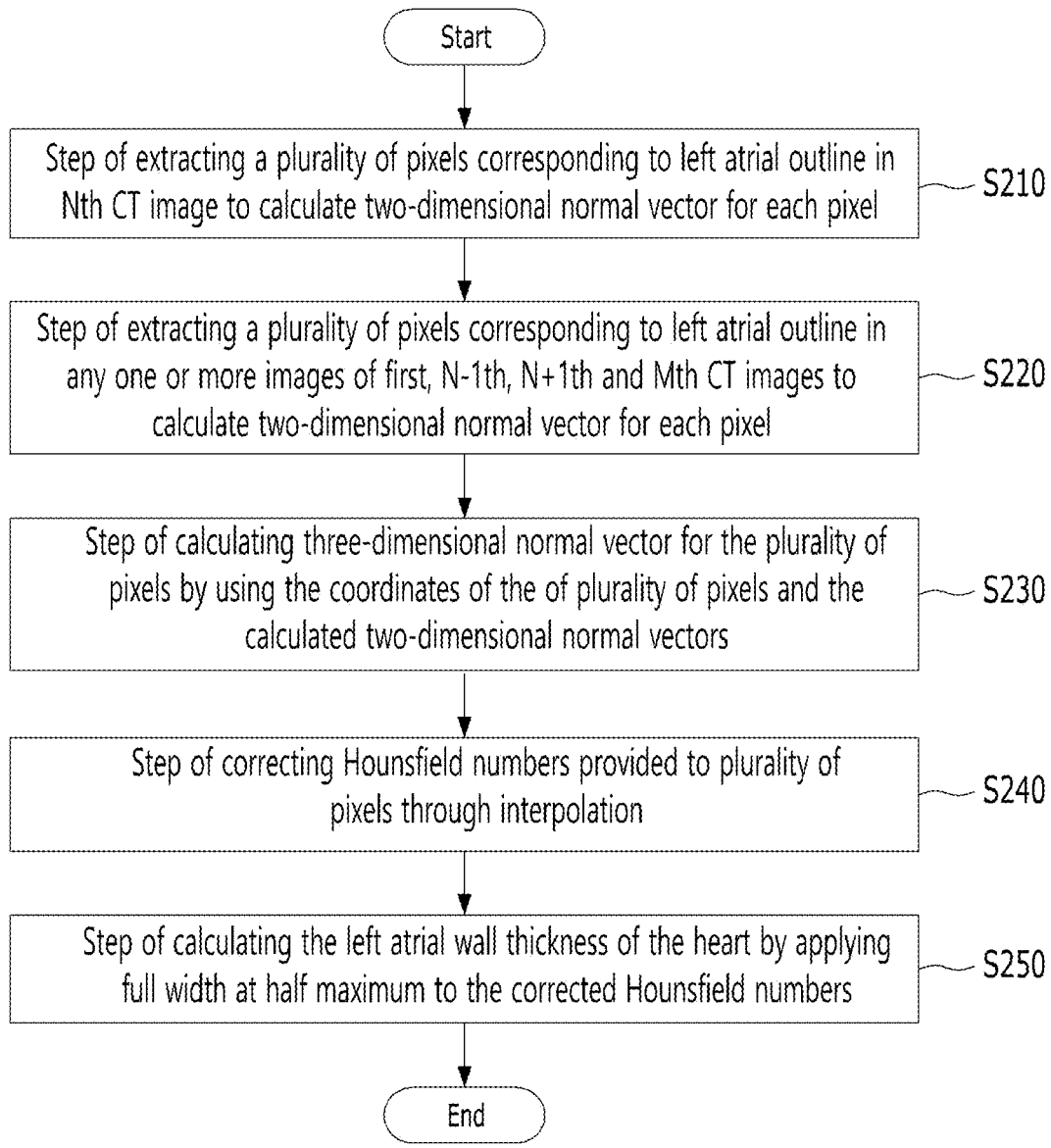
FIG. 2 is a flowchart showing representative steps in a measurement method for the left atrial wall thickness of the heart according to a second embodiment of the present invention.

FIG. 2 is a flowchart showing representative steps in the measurement method for the left atrial wall thickness of the heart according to the second embodiment of the present invention.

However, the second embodiment of the present invention is just a preferred embodiment to accomplish the objects of the present invention. If necessary, some steps may be added or deleted. Of course, one step may be included in another step.

On the other hand, all of the steps are performed by the measurement device 100 for the left atrial wall thickness of the heart according to the first embodiment of the present invention.

First, a plurality of pixels corresponding to the left atrial outline is extracted in an Nth (N is a positive integer greater than or equal to 3) computed tomography (CT) image having Hounsfield numbers applied by pixel, and a two-dimensional normal vector for each pixel is calculated (at step S210).

In this case, the computed tomography (CT), more commonly known as a CT scan is a medical imaging technique in which while x-rays are moved longitudinally between the upper and lower layers of an object to be imaged, they are transmitted to the object to obtain the information of cross-sectional images according to the transmission rates at given time points.

In the case of the CT images, the longitudinal direction of the object to be imaged has movements in parallel with the intercepts of all axes except a cross section in three-dimensional axes, but the interiors of the object to be imaged are not necessarily vertical to the longitudinal direction thereof. Accordingly, the direction of the normal vector of one pixel on the cross section of the object to be imaged may be different from the vertical direction of a real surface, which will be corrected by the three-dimensional normal vector as will be discussed later.

Figure 3:
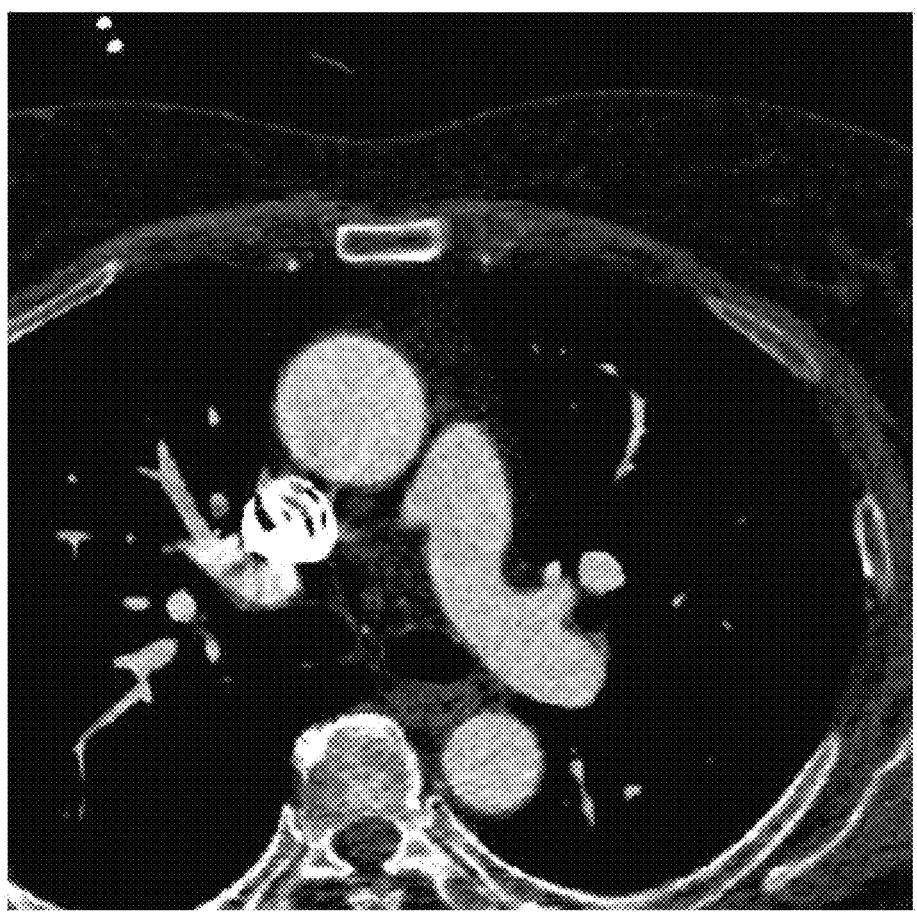
FIG. 3 is an exemplary computed tomography (CT) image of the heart.

FIG. 3 is an exemplary CT image of the heart. The heart and the interiors of the heart may be recognized somewhat by radiology specialists, but there is a little difficulty in accurately recognizing the left atrium of the heart.

The CT images include various information, but according to the present invention, Hounsfield numbers with 4096 steps, which are applied correspondingly to the pixel positions, are used.

The Hounsfield numbers, which are included in the CT image of the heart, may be used with the existing numbers, but in some cases, the pixel values, which are changed through given operations using a rescale intercept, a rescale slope, a window width value, and a window center value, may be used. For example, a display value is operated through a Hounsfield number*rescale slope+rescale intercept, and a changed pixel value is operated through the display value−(window center−0.5)/(window width−1)+0.5.

Figure 4:
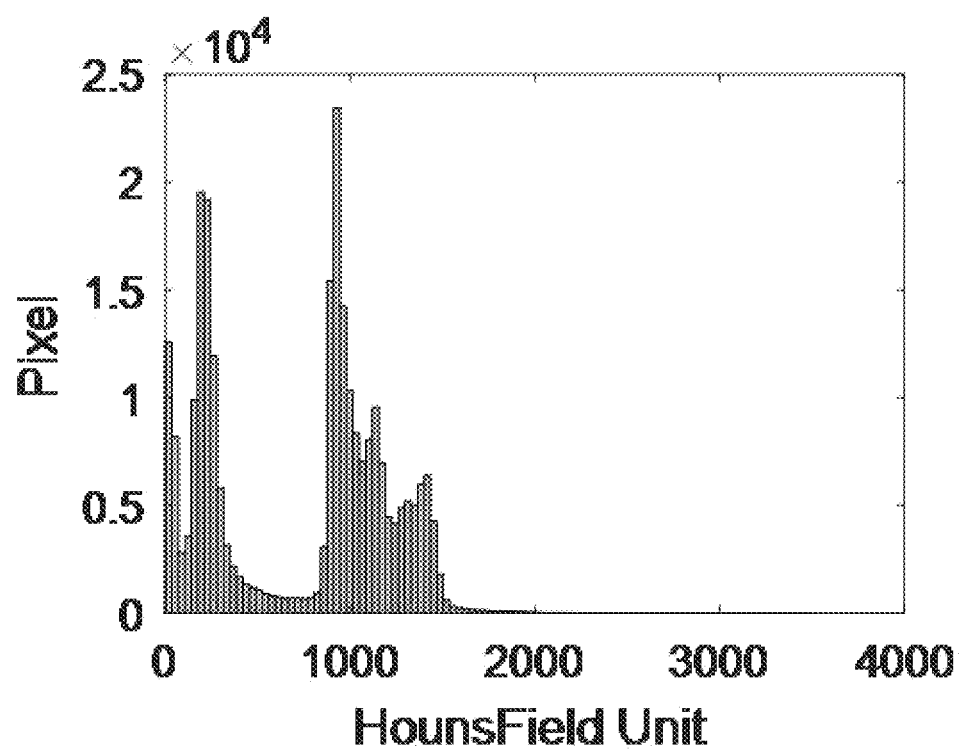
FIG. 4 is an exemplary histogram showing the Hounsfield numbers when the contrast medium is used for the left atrium.

On the other hand, the Hounsfield numbers may be varied according to the attenuation coefficients of the object to be imaged. If it is desired to measure the left atrial wall thickness, a contrast medium is used to thus apply the Hounsfield numbers having clear values to the left atrium, and FIG. 4 is an exemplary histogram showing the Hounsfield numbers when the contrast medium is used for the left atrium.

Referring back to FIG. 2, the explanation will be given again.

In the Nth CT image, the N is a positive integer greater than or equal to 3, and in this case, the CT is performed to obtain a plurality of CT images, while x-rays are being moved longitudinally between the upper and lower layers of the object to be imaged. Among the plurality of CT images, all CT images except a first CT image as a start image, an N−1th CT image, an N+1th CT image, and an Mth (M is a positive integer greater than or equal to 5) CT image as a finish image can be freely used. Further, the first CT image, the N−1th CT image, the N+1th CT image, and the Mth CT image may be separately used in measuring the thickness of the left atrium from the Nth CT image, and an explanation of the process will be given in detail below.

Figure 5:
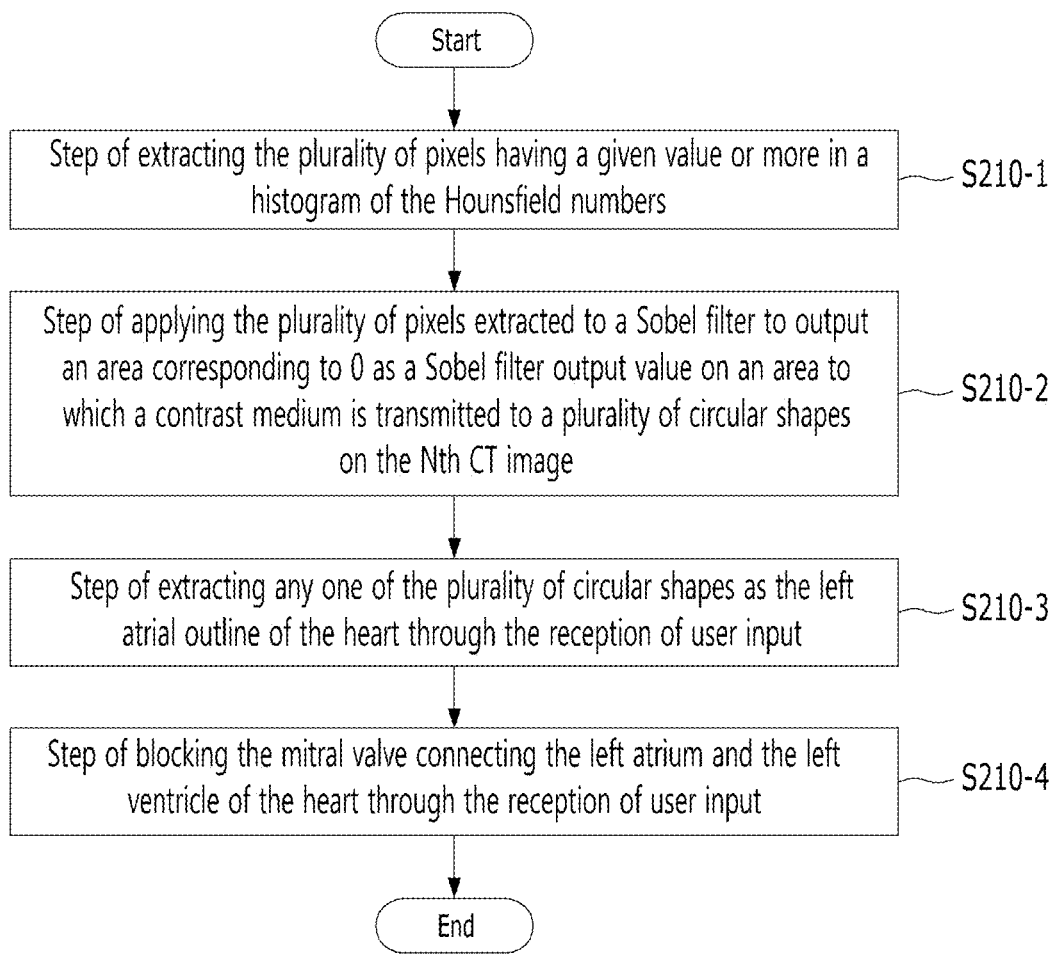
FIG. 5 is a flowchart showing detailed steps of step S210.

FIG. 5 is a flowchart showing detailed steps of step S210. However, the detailed steps are included in a preferred embodiment of the present invention to accomplish the objects of the present invention, and if necessary, some steps may be added or deleted. Of course, one step may be included in another step.

First, a plurality of pixels having a given value or more is extracted in a histogram of the Hounsfield numbers applied to a plurality of pixels included in the Nth CT image (at step S210-1).

In this case, the given value is freely set by a designer of the measurement device 100 for the left atrial wall thickness of the heart, and for example, the given value is set within the range of 500 to 780 before and after 640±140 in the histogram of the Hounsfield numbers. If the plurality of pixels is extracted, they are applied to a Sobel filter to output an area corresponding to 0 as a Sobel filter output value on an area to which a contrast medium is transmitted to a plurality of circular shapes on the Nth CT image (at step S210-2).

This forms a threshold section reversely to the Hounsfield numbers of the left atrium of the heart, thereby masking an unnecessary area. Accordingly, the Nth CT image is reversely produced.

Figure 6:
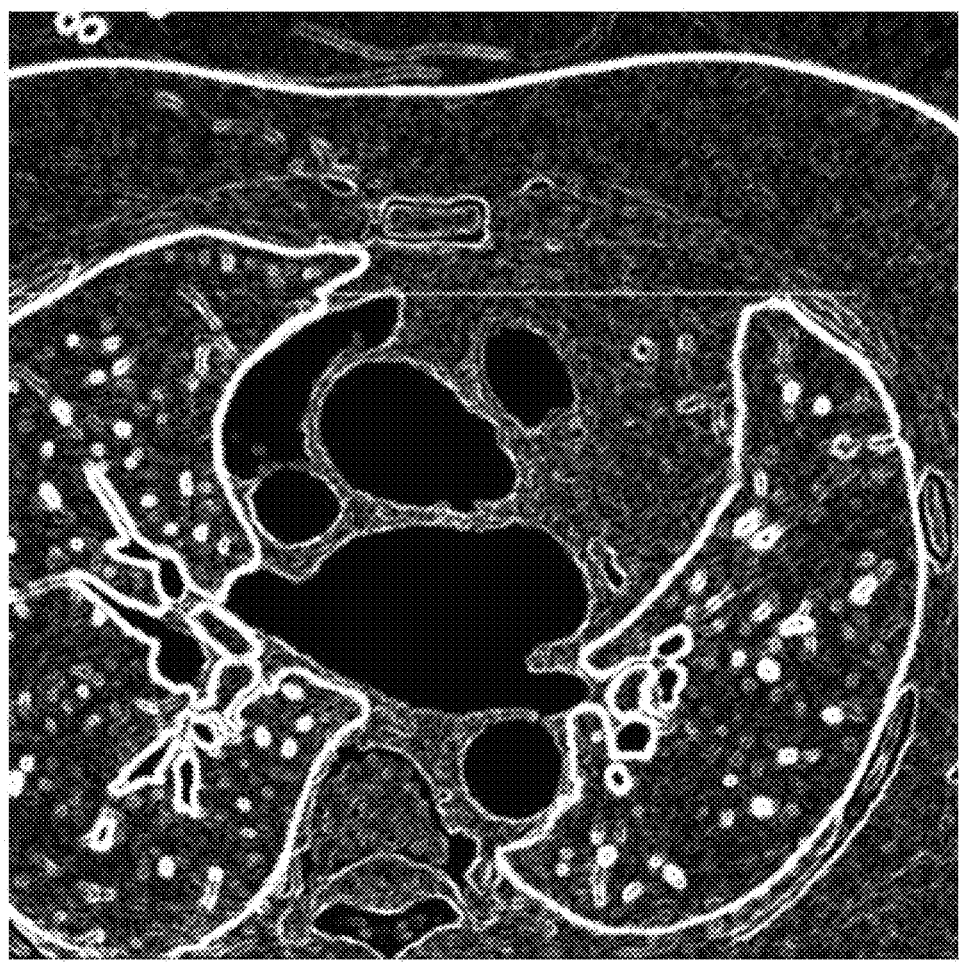
FIG. 6 is an exemplary view showing the area corresponding to 0 as a Sobel filter output value in a plurality of circular shapes on an Nth CT image.

In specific, the Sobel filter is a known filter that passes pixels within a radius of 3*3 around one pixel through kernels of Gx and Gy and organizes the pixels, and accordingly, the area to which the contrast medium is transmitted is masked with 0 as the output value of the Sobel filter, the result of which is exemplarily shown by the white solid line of FIG. 6. In this case, the Gx and Gy are expressed as follows:

$$G_x = \begin{bmatrix} +1 & 0 & -1 \\ +2 & 0 & -2 \\ +1 & 0 & -1 \end{bmatrix} * A$$

and $$G_y = \begin{bmatrix} +1 & +2 & +1 \\ 0 & 0 & 0 \\ -1 & -2 & -1 \end{bmatrix} * A,$$

$$G = \sqrt{G_x^2 + G_y^2}$$

If the window width value and the window center value are applied, in this case, the area to which the contrast medium is transmitted is more clearly recognized, but since the contrast medium is circulated through the circulation of the blood, only the Hounsfield numbers of the left atrium may not be clearly recognized. Accordingly, a correction step is additionally required.

After step S210-2, accordingly, any one of the plurality of circular shapes is extracted as the left atrial outline of the heart through the reception of user input (step S210-3). As shown in FIG. 6, any one of the plurality of circular shapes is manually selected as the outline of the area viewed as the left atrium of the heart, and in this case, desirably, the user is a person who has medical knowledge.

Figure 7:
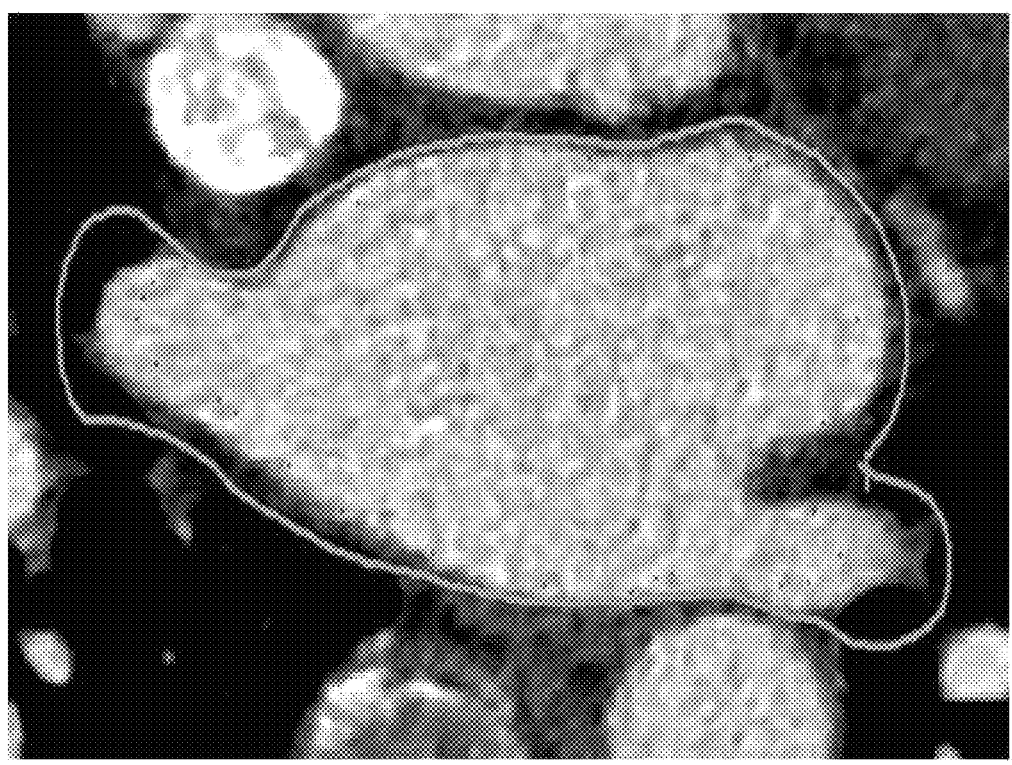
FIGS. 7 and 8 are exemplary views showing the area of the left atrium of the heart through the reception of user input.
Figure 8:
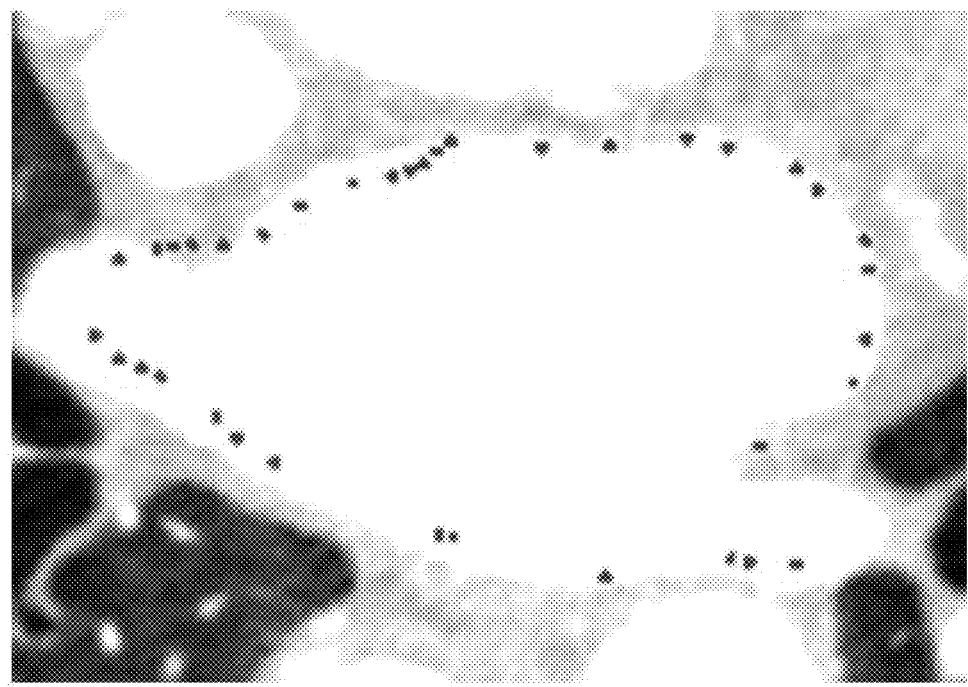

Further, the user input is received through a separate input part (not shown) included in the measurement device 100 or an input means such as a mouse connected to the measurement device 100, and exemplary views selected as the area of the left atrium of the heart through the reception of the user input are shown in FIG. 7 (by a white solid line) and FIG. 8 (by black points).

In this case, the user input is just an auxiliary means for extracting the area of the left atrium of the heart, and if the area is selected, the left atrial outline of the heart that is masked with 0 as the Sobel filter output value through crossing point verification is automatically extracted by the measurement device 100.

After step S210-3, further, a step of blocking the mitral valve connecting the left atrium and the left ventricle of the heart is performed, and when the left atrium of the heart is contracted, the blood moves to the left ventricle through the mitral valve. If the measurement method is performed only up to step 210-3, like a fish trap, the mitral valve may not be perfectly blocked.

After step S210-3, accordingly, the mitral valve connecting the left atrium and the left ventricle of the heart is blocked through the reception of user input (at step S210-4), and the explanation of the user input is given in the same manner as described above at step S210-3. For the brevity of the description, the detailed explanation is avoided, and in this case, FIG. 9 is an exemplary view showing the mitral valve blocked through the reception of the user input.

Figure 9:
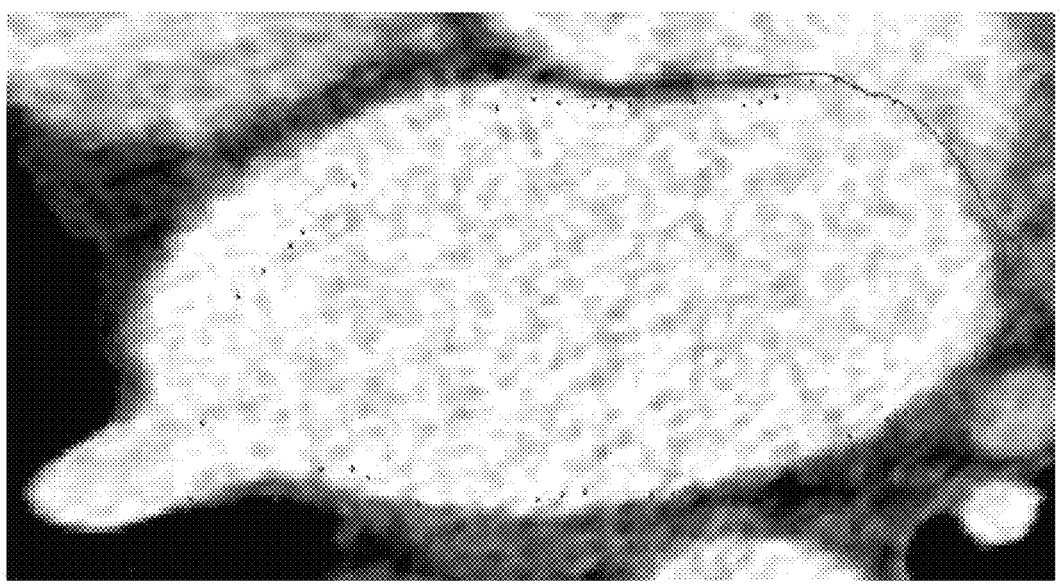
FIG. 9 is an exemplary view showing the mitral valve appearing through the reception of user input.

Referring to FIG. 9, it is checked that the mitral valve is displayed by a black solid line and block points, but in the same manner as step S210-3, of course, it is possible that only the black solid line or black points may be received through the user input.

Under steps S210-1 to S210-4 as mentioned above, the left atrial outline of the heart can be extracted, and hereinafter, a method for calculating a two-dimensional normal vector for each pixel will be explained.

Figure 10:
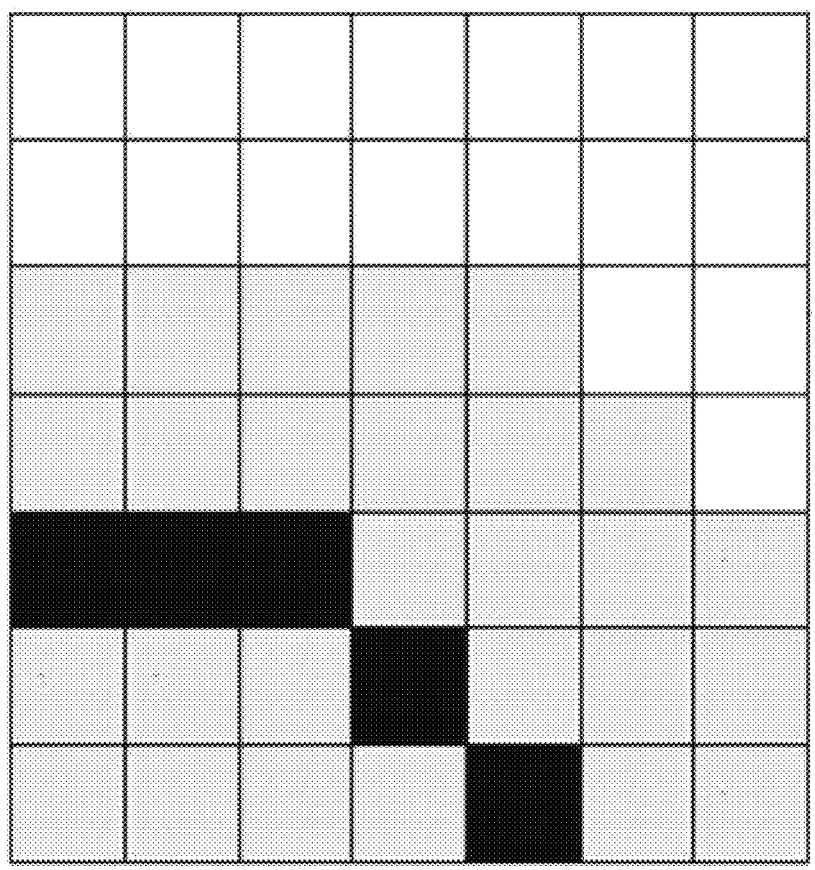
FIG. 10 is a diagram showing the left atrial outline of the heart, which is indicated in pixel units.
Figure 11:
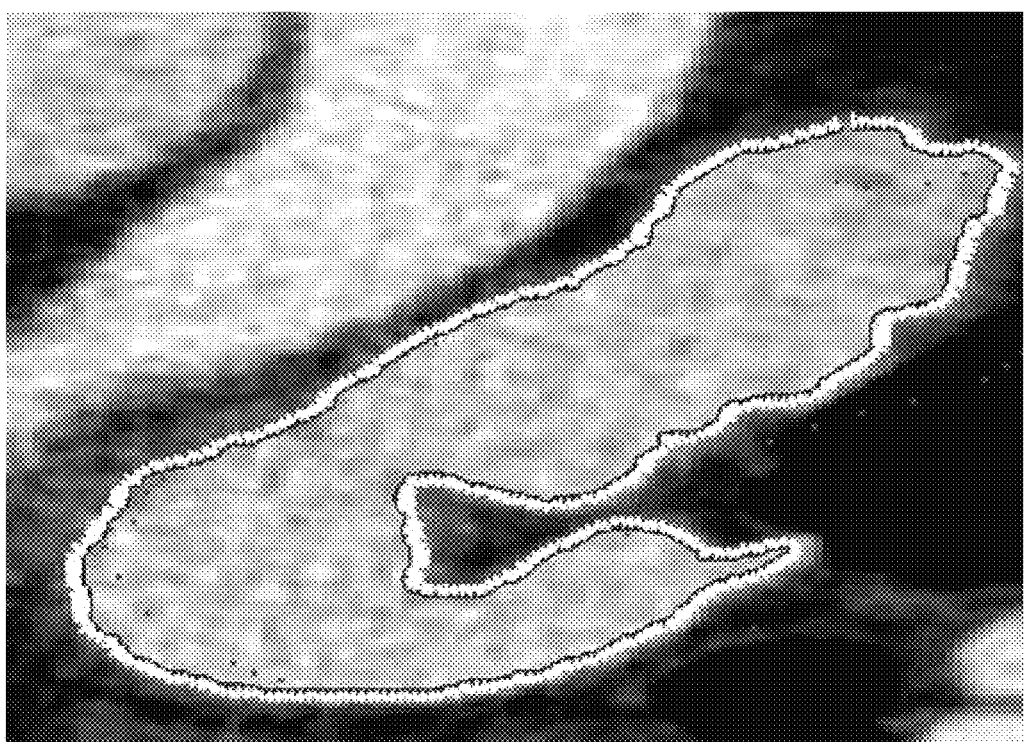
FIG. 11 is an exemplary view showing the CT image indicated with a plurality of pixels within a given range.

FIG. 10 is a diagram showing the left atrial outline of the heart, which is indicated in pixel units, and the black pixels in FIG. 10 correspond to the left atrial outline of the heart. The measurement device 100 searches a plurality of pixels within a given range with respect to the coordinates of the plurality of pixels corresponding to the left atrial outline of the heart, and in this case, the given range is any one of one pixel (3*3), two pixels (5*5), and two pixels (5*3) in left and right sides and one pixel in up and down sides in every direction, and FIG. shows one pixel (3*3) indicated by a gray color in every direction. Moreover, FIG. 11 is an exemplary view showing the CT image displayed with the plurality of pixels (the white area) within the given range with respect to the coordinates of the plurality of pixels corresponding to the extracted left atrial outline of the heart.

Accordingly, a new position may be produced to improve the accuracy of the left atrial outline of the heart in the Nth CT image, and if it is assumed that the black pixel corresponding to the initially extracted left atrial outline of the heart is P and the eight pixels around the corresponding pixel are P1 to P8, the new position is produced through (P+(the sum of the pixels selected among P1 to P8))/(the number of pixels selected+1). The two-dimensional normal vector for the new position is calculated through an operation between a position where the two-dimensional normal vector is calculated and the two points closest to the position. For example, if it is assumed that the new position is P' and the two points closest to the new position are P1' and P2', the two-dimensional normal vector is calculated by X: −(P'−P1')·y−(p2'−P')·y, Y: (P'−P1')·x+(p2'−P')·x. In the same manner as above, the two-dimensional normal vectors can be calculated for the respective pixels corresponding to the initially extracted left atrial outline of the heart.

If the two-dimensional normal vectors are calculated, a plurality of pixels corresponding to the left atrial outline is extracted in any one or more images of first, N−1th, N+1th, and Mth (M is a positive integer greater than or equal to 5) CT images, using the coordinates of the plurality of pixels corresponding to the left atrial outline extracted in the Nth CT image, and the two-dimensional normal vectors for the respective pixels are calculated (at step S220).

Figure 12:
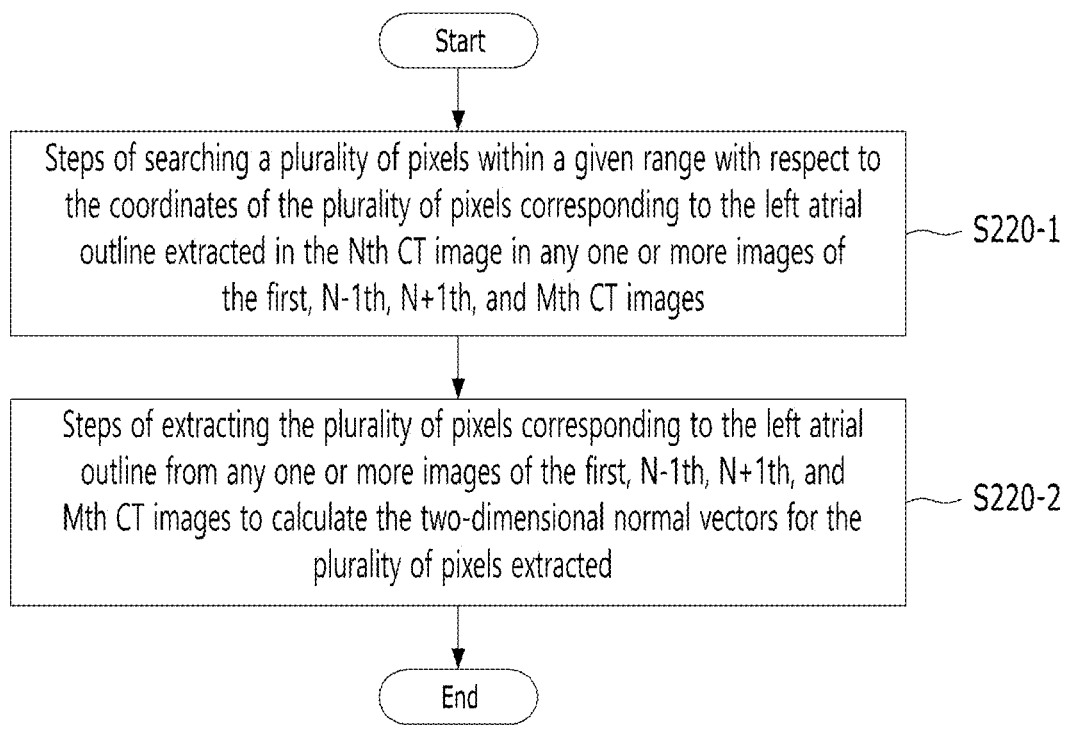
FIG. 12 is a flowchart showing detailed steps of step S220.

In this case, the coordinates of the plurality of pixels corresponding to the left atrial outline extracted in the Nth CT image may become the coordinates of the plurality of pixels corresponding to the left atrial outline extracted initially, but desirably, they can be the coordinates of the plurality of pixels determined through the new position, thereby improving the accuracy. FIG. 12 is a flowchart showing detailed steps of step S220. However, the detailed steps are included in a preferred embodiment of the present invention to accomplish the objects of the present invention, and if necessary, some steps may be added or deleted. Of course, one step may be included in another step.

First, a plurality of pixels within a given range with respect to the coordinates of the plurality of pixels corresponding to the left atrial outline extracted in the Nth CT image is searched in any one or more images of the first, N−1th, N+1th, and Mth CT images (at step S220-1).

As the left atrial outline of the heart is extracted in the Nth CT image, in specific, the coordinates of the plurality of pixels corresponding to the extracted left atrial outline can be extracted, and if the Nth CT image includes 512*512 pixels, the two dimensional coordinates (x and y) for the respective pixels can be extracted. Accordingly, the above steps are also applied to any one or more images of the first, N−1th, N+1th, and Mth CT images.

Further, the given range is any one of one pixel (3*3), two pixels (5*5), and two pixels (5*3) in left and right sides and one pixel in up and down sides in every direction, and the given range is applied to any one or more images of the first, N−1th, N+1th, and Mth CT images, thereby searching the plurality of pixels therewithin.

After that, the plurality of pixels corresponding to the left atrial outline is extracted in any one or more images of the first, N−1th, N+1th, and Mth CT images, using the coordinates of the plurality of pixels within the given range and the coordinates of the plurality of pixels corresponding to the left atrial outline extracted in the Nth CT image, and normal vectors in two dimension for the respective pixels are calculated (at step S220-2).

This is the step of producing a new position for improving the accuracy in the left atrial outline of the heart from any one or more images of the first, N−1th, N+1th, and Mth CT images to calculate the two-dimensional normal vectors for the respective pixels, in the same manner as above.

Figure 13:
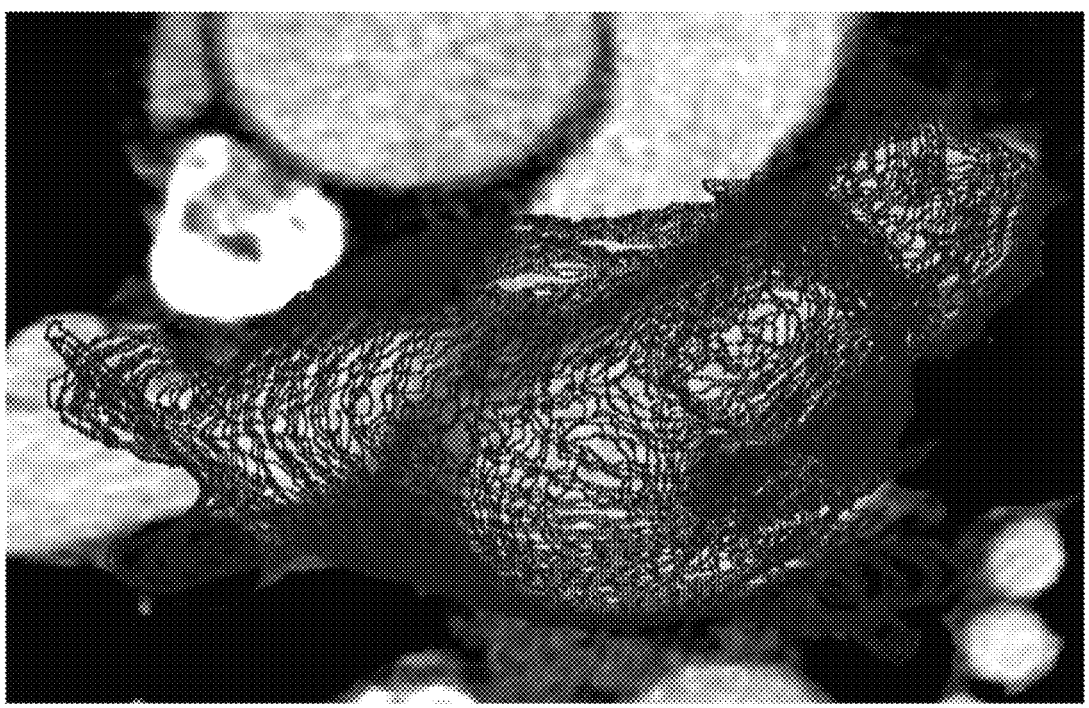
FIG. 13 is an exemplary view showing a three-dimensional left atrium model produced by accumulating first to Mth CT images.

Through steps S210 to S220 as mentioned above, the two-dimensional normal vectors are calculated for the respective pixels corresponding to the left atrial outline extracted in the Nth CT image, and the two-dimensional normal vectors are calculated for the respective pixels corresponding to the left atrial outline extracted in any one or more images of the first, N−1th, N+1th, and Mth CT images are calculated. If the first to Mth CT images are accumulatedly produced using the directions of the two-dimensional normal vectors, a three-dimensional left atrium model as shown in the center of FIG. 13 can be obtained. In the CT image, however, the interior of the object to be imaged may be not necessarily vertical to the longitudinal direction of the CT image, and accordingly, the normal vector direction of one pixel on the cross section of the object to be imaged is different from the vertical direction of the real surface. So as to allow the normal vector direction of one pixel on the cross section of the object to be imaged to correspond to the vertical direction of the real surface, further, the three-dimensional normal vector for the pixel has to be calculated. Now, an explanation of the calculation of the three-dimensional normal vector will be given.

Figure 14:
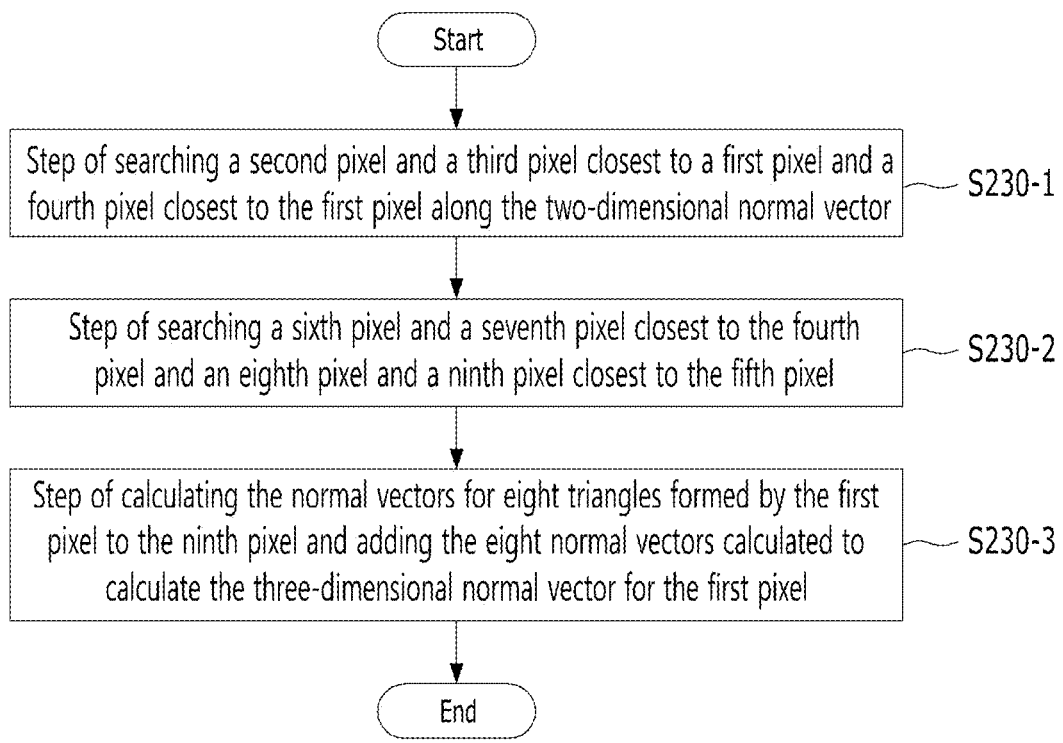
FIG. 14 is a flowchart showing detailed steps of step S230.

FIG. 14 is a flowchart showing detailed steps of step S230. However, the detailed steps are included in a preferred embodiment of the present invention to accomplish the objects of the present invention, and if necessary, some steps may be added or deleted. Of course, one step may be included in another step.

Figure 15:
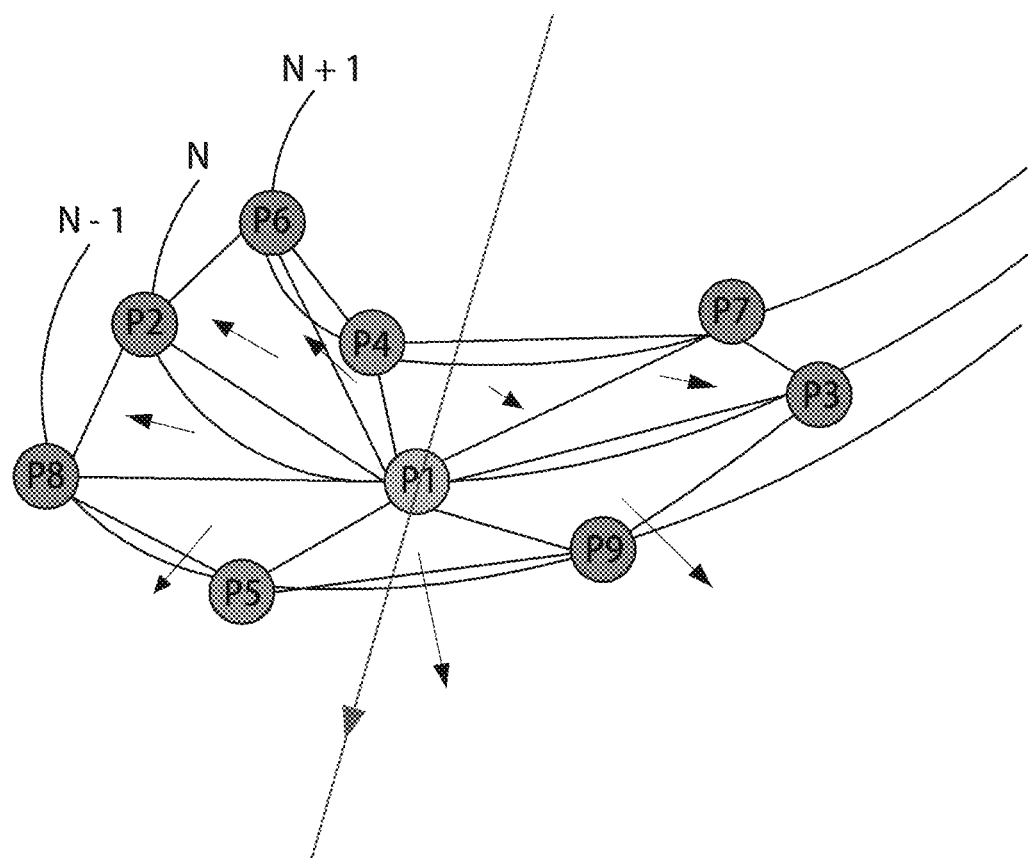
FIG. 15 is an exemplary view showing a plurality of pixels so as to help the explanation of a method for calculating the three-dimensional normal vectors for the plurality of pixels.
Figure 16:
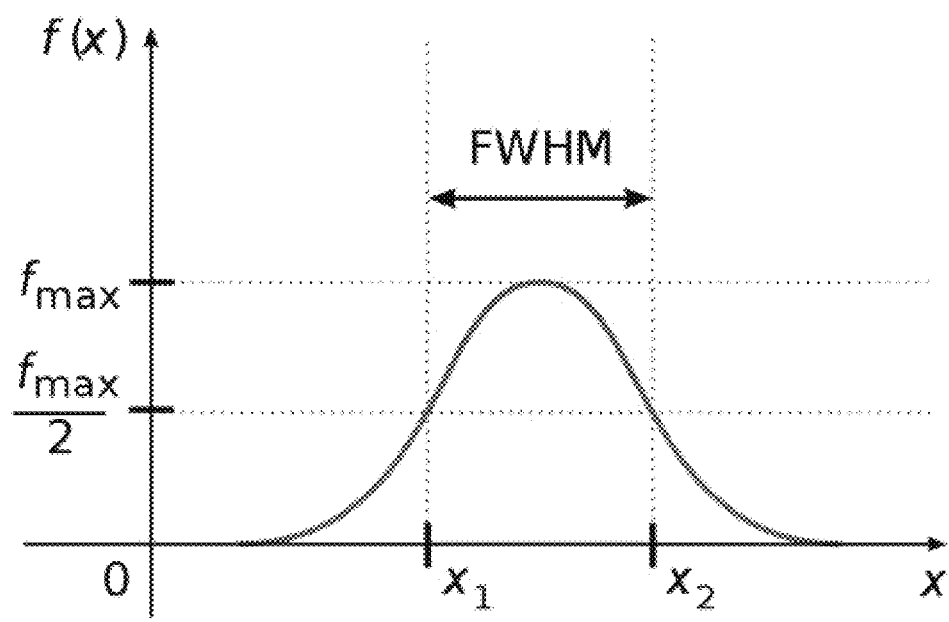
FIG. 16 is an exemplary view showing full width at half maximum.

Referring first to FIG. 15 in describing respective steps as shown in FIG. 14, there are provided a first pixel P1 (orange point) as any one of the plurality of pixels corresponding to the left atrial outline extracted in the Nth CT image, a second pixel P2 (blue point) and a third pixel P3 (blue point) closest to the first point P1, a fourth pixel P4 (green point) closest to the first pixel P1 in the N−1th CT image and a fifth pixel P5 (green point) closest to the first pixel P1 in the N+1th CT image along the two-dimensional normal vector calculated for the first pixel P1, a sixth pixel P6 (blue point) and a seventh pixel P7 (blue point) closest to the fourth pixel P4 in the N−1th CT image, and an eighth pixel P8 (blue point) and a ninth pixel P9 (blue point) closest to the fifth pixel P5 in the N+1th CT image.

First, the second pixel P2 and the third pixel P3 closest to the first pixel P1 as any one of the plurality of pixels corresponding to the left atrial outline extracted in the Nth CT image are searched, and the fourth pixel P4 closest to the first pixel P1 in the N−1th CT image and the fifth pixel P5 closest to the first pixel P1 in the N+1th CT image along the two-dimensional normal vector calculated for the first pixel P1 are searched (at step S230-1).

In this case, the closest pixel in one CT image indicates the pixel closest to any one of the plurality of pixels corresponding to the left atrial outline extracted, and since the CT image is a two dimensional image and the left atrial outline of the heart is a two dimensional outline, the pixels closest to the given pixel can be located around the given pixel. That is, the second pixel P2 and the third pixel P3, which are located near to the first pixel P1, may become the pixels closest to the first pixel P1 in the Nth CT image.

If any one of the plurality of pixels corresponding to the left atrial outline extracted in any one image of the pre-CT image and the post-CT image accurately corresponds to the direction of the two dimensional normal vector of any one of the plurality of pixels corresponding to the left atrial outline extracted in one CT image, the closest pixel may be the corresponding pixel, but if the closest pixel is not the corresponding pixel accurately, the pixel, which is closest to a point where the left atrial outlines extracted in the pre-CT image and the post-CT image are overlaid onto each other along the direction of the two dimensional normal vector, may be the corresponding pixel. FIG. 15 shows the example of the latter.

After that, the sixth pixel P6 and the seventh pixel P7 closest to the fourth pixel P4 in the N−1th CT image are searched, and the eighth pixel P8 and the ninth pixel P9 closest to the fifth pixel P5 in the N+1th CT image are searched (at step S230-2).

This step is also performed to search the closest pixels from one CT image, and accordingly, the explanation as mentioned above is given in the same manner.

If the first pixel P1 to the ninth pixel P9 are determined, normal vectors for eight triangles formed by the first pixel P1 to the ninth pixel P9 are calculated, and the eight normal vectors calculated are added to calculate the three-dimensional normal vector for the first pixel P1 (at step S230-3).

As the determined pixels are nine, the eight triangles among the determined pixels can be formed, and since the coordinates of the three pixels constituting the corresponding triangle are all recognized, further, the normal vector of the corresponding triangle can be easily calculated through an outer product. For example, if one triangle is constituted of the first pixel P1, the third pixel P3, and the seventh pixel p7, V1=P3−P1 and V2=P7−P1. Accordingly, the normal vector of the triangle is calculated by V1×V2. FIG. 15 shows the calculated normal vectors with black arrows.

If the normal vectors for the eight triangles are all added, the three-dimensional normal vector for the first pixel P1 is calculated, which is shown with a red arrow in FIG. 15.

In the same manner as above, the three-dimensional normal vectors can be calculated for the plurality of pixels corresponding to the left atrial outline extracted in the Nth CT image except the first pixel P1 (which has been already calculated) and the plurality of pixels corresponding to the left atrial outline extracted in any one or more images of the first, N−1th, N+1th, and Mth CT images. That is, the three-dimensional normal vectors can be calculated for the plurality of pixels corresponding to the left atrial outline extracted in the first to Mth CT images.

In the explanation of step S210, the Hounsfield numbers among various information included in the CT image are used in measuring the left atrial wall thickness of the heart, and so as to allow the normal vector direction of one pixel on the cross section of the object to be imaged to correspond to the vertical direction of the real surface, the Hounsfield numbers included in the initial CT image have to be corrected with the three-dimensional normal vector for each pixel, thereby ensuring accurate measurement results.

Now, an explanation will be returned to FIG. 2.

If the three-dimensional normal vectors are calculated, the Hounsfield numbers, which are provided to the plurality of pixels corresponding to the directions of the three-dimensional normal vectors for the respective pixels, are corrected using interpolation (at step S240).

In this case, the interpolation means trilinear interpolation, and the directions of the three-dimensional normal vectors for the respective pixels are defined in a three-dimensional space. In this case, since the Nth CT image, the N−1th CT image, and the N+1th CT image are viewed in the three-dimensional space with grids, the trilinear interpolation is desirably applied.

In this case, if it is assumed that the coordinates of any one of the plurality of pixels corresponding to the directions of the three-dimensional normal vectors for the respective pixels are x, y, and z, the corrected Hounsfield numbers can be defined according to $f(x, y, z) \approx a0 + a1x + a2y + a3z + a4xy + a5xz + a6yz + a7xyz$ (wherein represents an approximate value), and in this case, a0 to a7 can be defined by the following matrix.

$$\begin{bmatrix} 1 & x0 & y0 & z0 & x0y0 & x0z0 & y0z0 & x0y0z0 \\ 1 & x1 & y0 & z0 & x1y0 & x1z0 & y0z0 & x1y0z0 \\ 1 & x0 & y1 & z0 & x0y1 & x0z0 & y1z0 & x0y1z0 \\ 1 & x1 & y1 & z0 & x1y1 & x1z0 & y1z0 & x1y1z0 \\ 1 & x0 & y0 & z1 & x0y0 & x0z1 & y0z1 & x0y0z1 \\ 1 & x1 & y0 & z1 & x1y0 & x1z1 & y0z1 & x1y0z1 \\ 1 & x0 & y1 & z1 & x0y1 & x0z1 & y1z1 & x0y1z1 \\ 1 & x1 & y1 & z1 & x1y1 & y1z1 & y1z1 & x1y1z1 \end{bmatrix} \begin{bmatrix} a0 \\ a1 \\ a2 \\ a3 \\ a4 \\ a5 \\ a6 \\ a7 \end{bmatrix} = \begin{bmatrix} c000 \\ c100 \\ c010 \\ c110 \\ c001 \\ c101 \\ c011 \\ c111 \end{bmatrix}$$

In this case, x, y, and z are respective coordinate axes, and 0 and 1 represent a pre-pixel and a post-pixel. Further, cijk (I, j, k=0 or 1) are values of the pixels located on xi, yj, and zk. For example, if the positions of the pixels to which the interpolation is applied are 1.5, 2.5, and 5.5, x0, y0 and z0 are 1, 2, and 5, and if the calculation is carried out per one pixel, x1, y1 and z1 are 2, 3, and 6. Further, C000 is a pixel value of (1, 2, 5), and c111 is of (2, 3, 6).

If the same method as above is performed for the plurality of pixels corresponding to the left atrial outline extracted in the Nth CT image and for the plurality of pixels corresponding to the left atrial outline extracted in any one or more images of the first, N−1th, N+1th, and Mth CT images, the Hounsfield numbers for the respective pixels can be corrected.

If the Hounsfield numbers are corrected, full width at half maximum (FWHM) is applied to the corrected Hounsfield numbers to thus calculate the left atrial wall thickness of the heart (at step S250).

In this case, the FWHM is a known technique for calculating a thickness with ease to thus select half of the two opposite points having irradiance opposite to each other, and when the two opposite points having irradiance opposite to each other are selected, half of the values is selected so that as the acquired width is half of the entire width, it is called "full width at half maximum". This is exemplarily shown in FIG. 16.

Figure 17:
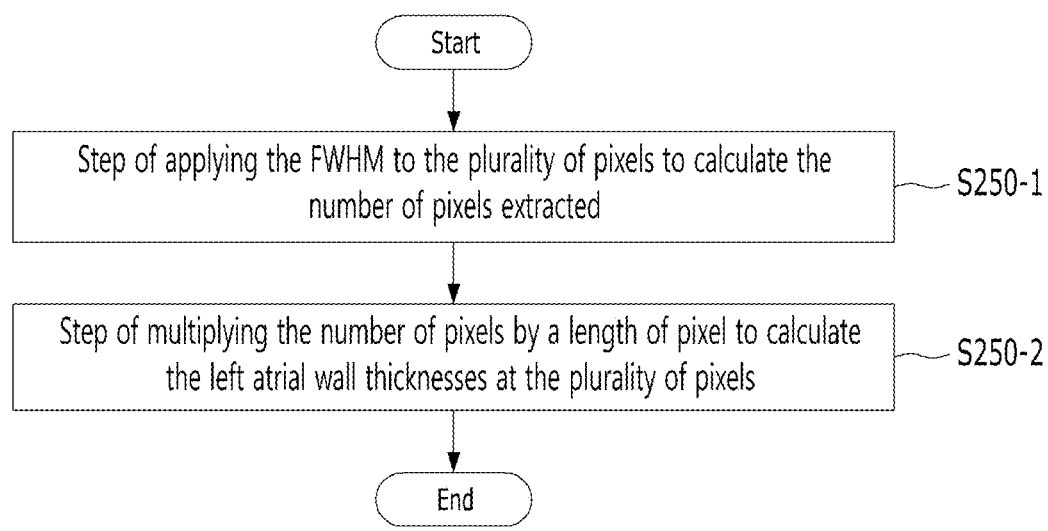
FIG. 17 is a flowchart showing detailed steps of step S250.

FIG. 17 is a flowchart showing detailed steps of step S250. However, the detailed steps are included in a preferred embodiment of the present invention to accomplish the objects of the present invention, and if necessary, some steps may be added or deleted. Of course, one step may be included in another step.

First, the FWHM is applied to the respective pixels, the pixels to which the FWHM is applied are extracted, and the number of pixels extracted is calculated (at step S250-1).

Figure 18:
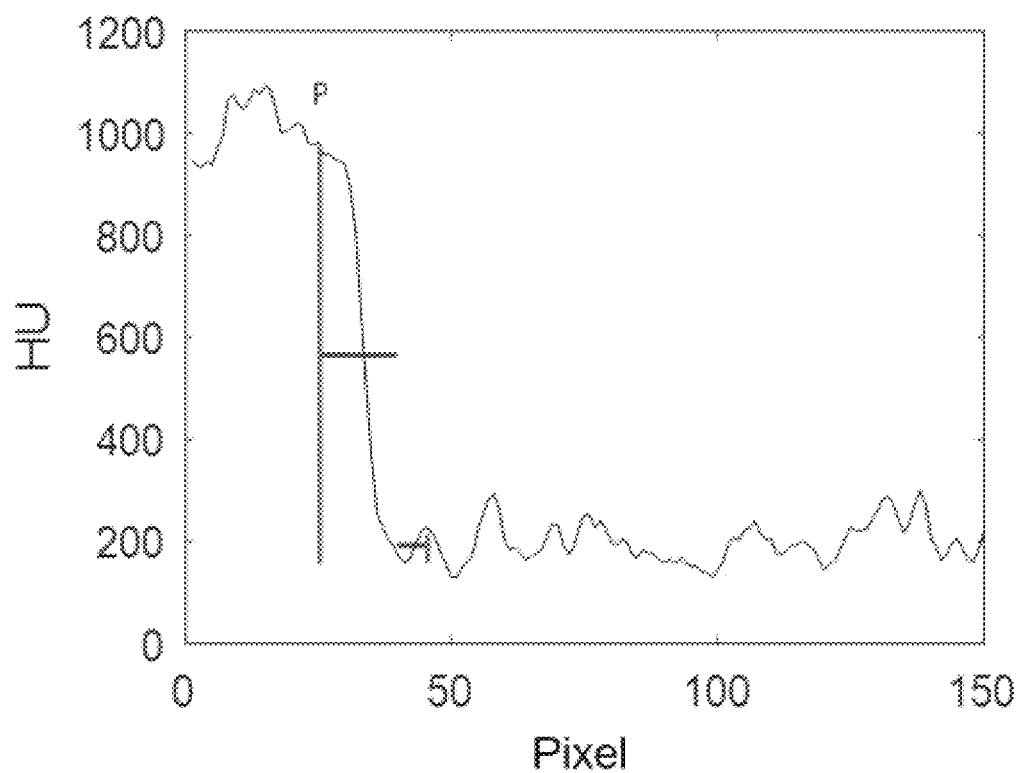
FIG. 18 is an exemplary graph showing the corrected Hounsfield numbers for the plurality of pixels corresponding to one another toward the direction of a three-dimensional normal vector of a specific pixel.

FIG. 18 is an exemplary graph showing the corrected Hounsfield numbers for the plurality of pixels corresponding to one another toward the direction of the three-dimensional normal vector of a specific pixel. If it is desired to measure the left atrial wall thickness of the heart at a point A by a user, 35 pixels are calculated at a point B as half of the line up to a point where the inclination of the graph is opposite along the graph from the point A, and 45 pixels are calculated at a point C as half of the line up to a point where the inclination of the graph is opposite again from the point where the inclination of the graph is opposite. Next, 10 pixels, which are difference between the number of pixels at the point B and the number of pixels at the point C, are calculated.

In this case, the points where the inclinations of the graph are opposite to each other are the two opposite points having irradiance opposite to each other which are described in the FWHM.

If the number of pixels is calculated, it is multiplied by a length of pixel, so that the left atrial wall thicknesses of the heart at the respective pixels can be calculated (at step S250-2).

In this case, the length of the pixel is 0.4434 mm, but of course, it may be different according to the CT images. As the length of the pixel is multiplied by the number of pixels, the left atrial wall thickness as the cross section of the left atrium can be calculated. As shown in FIG. 18, accordingly, the left atrial wall thickness of the heart at the point A is 4.434 mm.

Further, only if the point is included in the left atrial area of the heart, the left atrial wall thickness of the heart can be calculated through the method as mentioned above, and in this case, if a specific point whose thickness is to be calculated is just inputted by the user, the left atrial wall thickness at the specific point can be in real time calculated by means of the measurement device 100 according to the present invention.

Up to now, the measurement device 100 for the left atrial wall thickness of the heart according to the first embodiment of the present invention and the measurement method for the left atrial wall thickness of the heart according to the second embodiment of the present invention have been explained. Through the simple input of the user, according to the present invention, the left atrial wall thickness can be measured simply, quickly and accurately by the measurement device 100, so that optimal effects in radiofrequency catheter ablation can be obtained. Moreover, a relatively low expense is needed, without any additional test, and accordingly, in the case of a patient with heart arrhythmia, his or her left atrial wall thickness can be measured using the CT image, thereby minimizing the financial burden of his or her medical expense.

Further, the measurement method for the left atrial wall thickness of the heart according to the second embodiment of the present invention may be performed through a computer program stored in a recording medium and thus executed in a computer.

For the brevity of the description, an explanation of the measurement method carried out through the computer program will be not given in detail, but the computer program stored in the recording medium performs the same steps as carried out by the measurement device 100 according to the second embodiment of the present invention, thereby providing the same effectiveness. For example, the computer program stored in the recording medium is combined to a computing device to perform the steps of extracting a plurality of pixels corresponding to the left atrial outline of the heart from an Nth (N is a positive integer greater than or equal to 3) CT image having the Hounsfield numbers applied by pixel to calculate two-dimensional normal vectors for the pixels, extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the pixels, calculating the three-dimensional normal vectors for the pixels corresponding to the left atrial outline extracted in the Nth CT image and for the pixels corresponding to the left atrial outline extracted in any one or more images of the first, N−1th, N+1th, and Mth CT images, using the coordinates of the pixels and the calculated two-dimensional normal vectors, correcting Hounsfield numbers provided to the plurality of pixels corresponding to the directions of the three-dimensional normal vectors for the pixels through interpolation, and calculating the left atrial wall thickness of the heart by applying full width at half maximum (FWHM) to the corrected Hounsfield numbers.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A measurement method for the left atrial wall thickness of the heart through a left atrial wall thickness measurement device, the measurement method comprising the steps of:
   (a) extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted;
   (b) extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted;
   (c) calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors;
   (d) correcting the Hounsfield numbers provided to the plurality of pixels corresponding to the directions of the three-dimensional normal vectors for the plurality of pixels through interpolation; and
   (e) calculating the left atrial wall thickness of the heart by applying full width at half maximum (FWHM) to the corrected Hounsfield numbers.

2. The measurement method according to claim 1, wherein the step (a) comprises the steps of:
   (a-1) extracting the plurality of pixels having a given value or more in a histogram of the Hounsfield numbers applied to the plurality of pixels included in the Nth CT image;
   (a-2) applying the plurality of pixels extracted to a Sobel filter to output an area corresponding to 0 as a Sobel filter output value on an area to which a contrast medium is transmitted to a plurality of circular shapes on the Nth CT image; and
   (a-3) extracting any one of the plurality of circular shapes as the left atrial outline of the heart through the reception of user input.

3. The measurement method according to claim 2, further comprising the step of, after the step (a-3), extracting and blocking the mitral valve connecting the left atrium and the left ventricle of the heart through the reception of user input.

4. The measurement method according to claim 1, wherein the step (b) comprises the steps of:
   (b-1) searching a plurality of pixels within a given range with respect to the coordinates of the plurality of pixels corresponding to the left atrial outline extracted in the Nth CT image in any one or more images of the first, N−1th, N+1th, and Mth CT images; and
   (b-2) extracting the plurality of pixels corresponding to the left atrial outline from any one or more images of the first, N−1th, N+1th, and Mth CT images, using the coordinates of the plurality of pixels within the given range searched and the coordinates of the plurality of pixels corresponding to the left atrial outline extracted in the Nth CT image to calculate the two-dimensional normal vectors for the plurality of pixels extracted.

5. The measurement method according to claim 4, wherein the given range is any one of one pixel (3*3), two pixels (5*5), and two pixels (5*3) in left and right sides and one pixel in up and down sides in every direction with respect to the coordinates of the plurality of pixels corresponding to the left atrial outline extracted in the Nth CT image.

6. The measurement method according to claim 1, wherein the step (c) comprises the steps of:
   (c-1) searching a second pixel and a third pixel closest to a first pixel as any one of the plurality of pixels corresponding to the left atrial outline extracted in the Nth CT image and searching a fourth pixel closest to the first pixel in the N−1th CT image and a fifth pixel closest to the first pixel in the N+1th CT image along the two-dimensional normal vector calculated for the first pixel;
   (c-2) searching a sixth pixel and a seventh pixel closest to the fourth pixel in the N−1th CT image and searching an eighth pixel and a ninth pixel closest to the fifth pixel in the N+1th CT image; and (c-3) calculating the normal vectors for eight triangles formed by the first pixel to the ninth pixel and adding the eight normal vectors calculated to calculate the three-dimensional normal vector for the first pixel.

7. The measurement method according to claim 6, further comprising the step of performing the steps (c-1) to (c-3) for the plurality of pixels corresponding to the left atrial outline extracted in the Nth CT image and for the plurality of pixels corresponding to the left atrial outline extracted in any one or more images of the first, N−1th, N+1th, and Mth CT images, except the first pixel.

8. The measurement method according to claim 1, wherein the interpolation at the step (d) is trilinear interpolation.

9. The measurement method according to claim 1, wherein the step (e) comprises the steps of:
    (e-1) applying the FWHM to the plurality of pixels to calculate the number of pixels extracted; and
    (e-2) multiplying the number of pixels by a length of pixel to calculate the left atrial wall thicknesses at the plurality of pixels.

10. The measurement method according to claim 1, the length of pixel is 0.4434 mm.

11. A measurement device for the left atrial wall thickness of the heart, comprising:
    one or more processors;
    a network interface;
    a memory for loading computer programs executed by the processors; and
    a storage for storing large scale network data and the computer programs,
    wherein the computer programs perform:
    an operation (a) for extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted;
    an operation (b) for extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted;
    an operation (c) for calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors;
    an operation (d) for correcting the Hounsfield numbers provided to the plurality of pixels corresponding to the directions of the three-dimensional normal vectors for the plurality of pixels through interpolation; and
    an operation (e) of calculating the left atrial wall thickness of the heart by applying full width at half maximum (FWHM) to the corrected Hounsfield numbers.

12. A computer program stored in a medium and combined to a computing device to perform the steps of:
    (a) extracting a plurality of pixels corresponding to the left atrial outline in an Nth (N is a positive integer greater than or equal to 3) computed tomography (CT) image having Hounsfield numbers applied by pixel to calculate the two-dimensional normal vectors for the plurality of pixels extracted;
    (b) extracting a plurality of pixels corresponding to the left atrial outline from any one or more images of first, N−1th, N+1th, and Mth (M is a positive integer greater than or equal to 5) CT images, using the coordinates of the plurality of pixels corresponding to the left atrial outline extracted in the Nth CT image, to calculate the two-dimensional normal vectors for the plurality of pixels extracted;
    (c) calculating the three-dimensional normal vectors for the plurality of pixels corresponding to the left atrial outline extracted in the Nth CT image and for the plurality of pixels corresponding to the left atrial outline extracted in any one or more images of the first, N−1th, N+1th, and Mth CT images, using the coordinates of the plurality of pixels and the calculated two-dimensional normal vectors;
    (d) correcting the Hounsfield numbers provided to the plurality of pixels corresponding to the directions of the three-dimensional normal vectors for the plurality of pixels through interpolation; and
    (e) calculating the left atrial wall thickness of the heart by applying full width at half maximum (FWHM) to the corrected Hounsfield numbers.

* * * * *